United States Patent [19]

Adams et al.

[11] Patent Number: 4,647,220

[45] Date of Patent: Mar. 3, 1987

[54] METHOD OF AND APPARATUS FOR DETECTING CORROSION UTILIZING INFRARED ANALYSIS

[75] Inventors: Mark J. Adams, Kennesaw; Elton M. Crisman, Jr., Blairsville, both of Ga.

[73] Assignee: Lockheed Corporation, Calabasas, Calif.

[21] Appl. No.: 629,069

[22] Filed: Jul. 9, 1984

[51] Int. Cl.$^4$ .................... G01N 25/72; G01N 17/00
[52] U.S. Cl. .......................................... 374/5; 374/57; 374/124; 374/137
[58] Field of Search ............... 374/57, 124, 121, 4, 374/5, 6, 7, 43, 44, 137; 250/341

[56] References Cited

U.S. PATENT DOCUMENTS

| | | | |
|---|---|---|---|
| 2,879,401 | 3/1959 | Chicurel | 374/121 |
| 3,378,685 | 4/1968 | Green et al. | 250/341 |
| 3,413,474 | 11/1968 | Freeh | 374/7 |
| 3,427,861 | 2/1969 | Maley | 374/124 |
| 3,433,052 | 3/1969 | Maley | 374/124 |
| 3,451,254 | 6/1969 | Maley | 374/124 |
| 3,499,153 | 3/1970 | Stanfill, III | 374/4 |
| 3,583,223 | 6/1971 | Olsson | 374/7 |
| 3,681,970 | 8/1972 | Wells | 374/5 |
| 3,808,439 | 4/1974 | Renius | 250/341 |
| 3,864,958 | 2/1975 | Dreitzler | 374/4 |
| 4,304,995 | 12/1981 | Huttunen et al. | 250/341 |
| 4,343,182 | 8/1982 | Pompei | 374/124 |
| 4,365,307 | 12/1982 | Tatsuwaki et al. | 374/124 |
| 4,413,324 | 11/1983 | Tatsuwaki et al. | 356/45 |
| 4,417,822 | 11/1983 | Stein et al. | 374/125 |
| 4,429,225 | 1/1984 | Fumoto et al. | 250/341 |
| 4,468,136 | 8/1984 | Murphy et al. | 374/124 |
| 4,557,607 | 12/1985 | Busse | 374/121 |

Primary Examiner—Charles Frankfort
Assistant Examiner—Thomas B. Will
Attorney, Agent, or Firm—Stanley L. Tate

[57] ABSTRACT

A method and apparatus for the non-destructive identification and location of subcoating corrosion on a coated metal surface employing infrared thermography. The apparatus comprises a heat source for directing pulsed infrared radiation onto a test surface; a scanner for scanning the test surface for infrared radiation being emitted therefrom; a detector for capturing said emitted radiation and converting it into a signal representative of the thermal characteristics of the surface; and video display apparatus for visually displaying the signal as a thermal map of the surface. The method comprises the steps irradiating a test surface and detecting temperature differentials that occur on the irradiated surface.

22 Claims, 10 Drawing Figures

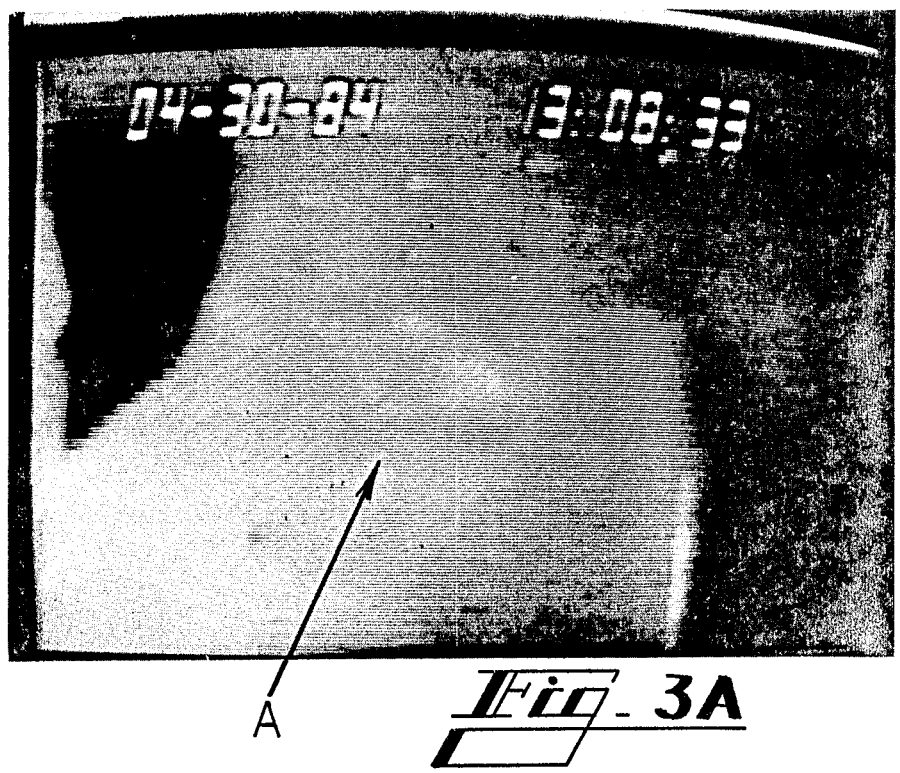
Fig_ 3A
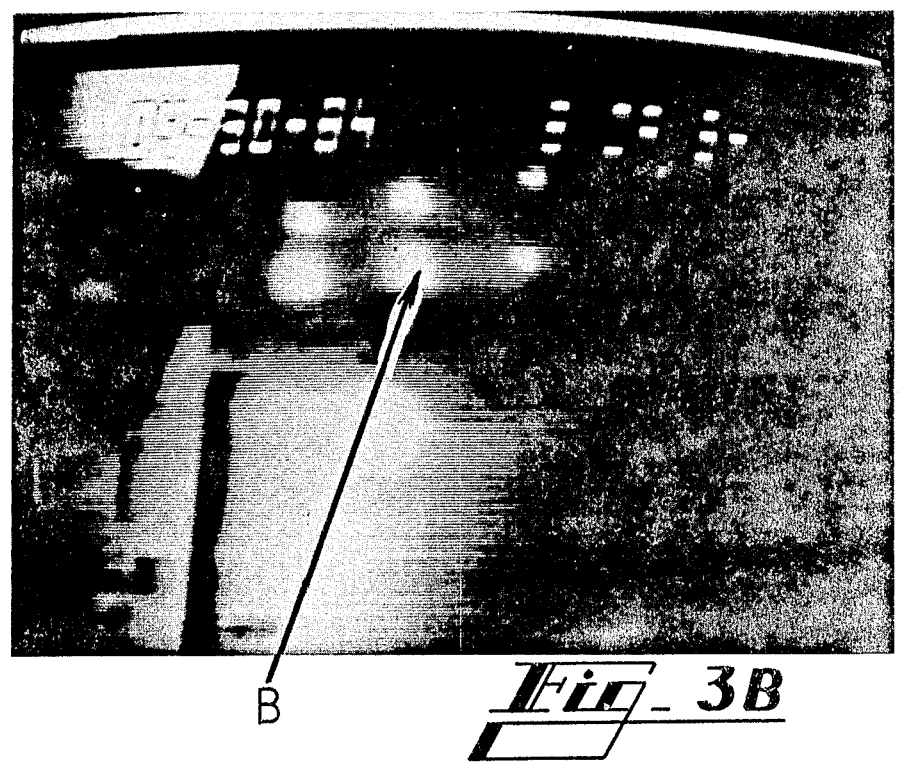
Fig_ 3B

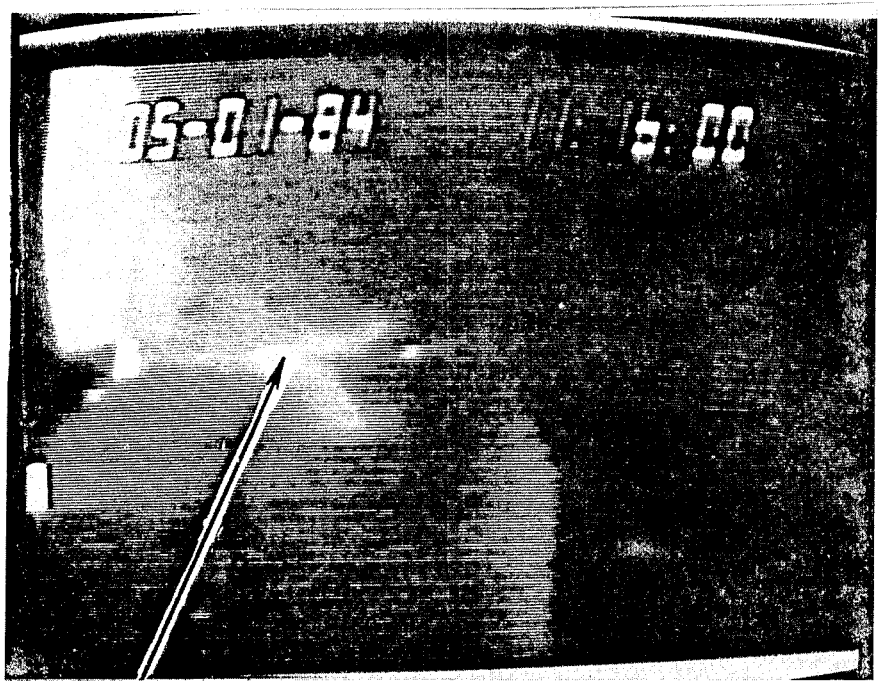
Fig_4A
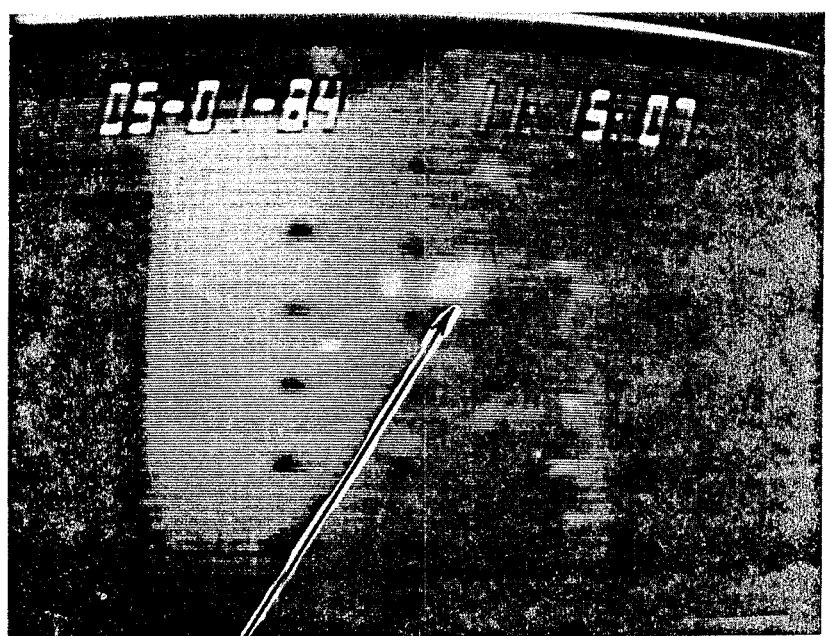
Fig_4B

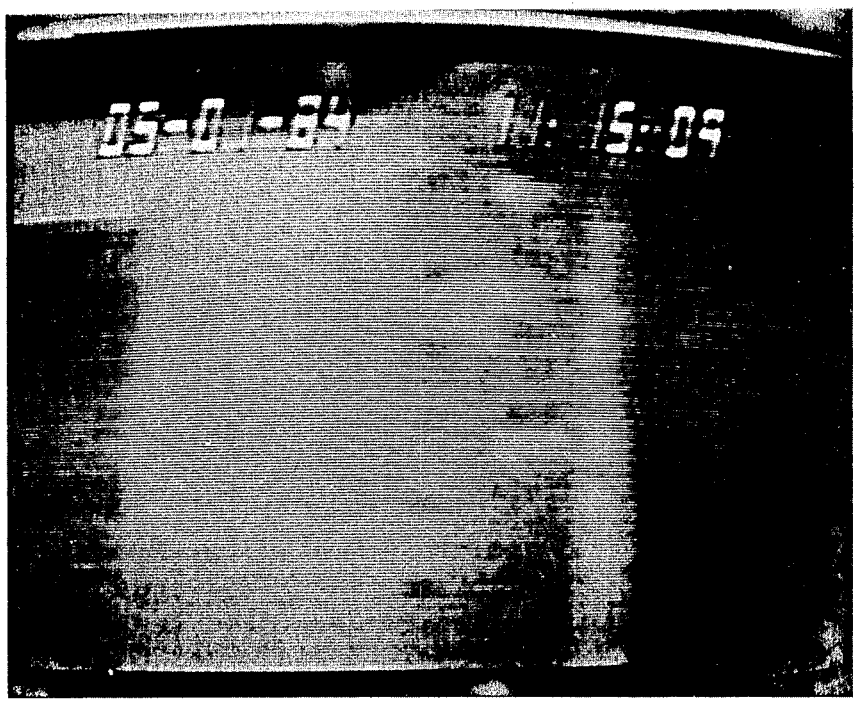
Fig_4C

METHOD OF AND APPARATUS FOR DETECTING CORROSION UTILIZING INFRARED ANALYSIS

TECHNICAL FIELD

This invention generally relates to a method of and apparatus for detecting corrosion in painted metal structures and more particularly to a method of and apparatus for utilizing infrared analysis to detect the temperature differential caused by the difference in thermal conductives of corroded metal and uncorroded metal.

BACKGROUND ART

Environmentally accelerated degradation and equipment failure are major problems in the maintenance of aerospace systems. Airborne agents, such as moisture (as rain, snow, condensation, humidity) pollutants (sulfur dioxide, nitrogen oxides, ozone, sand, dust, others, particularly wind, and solar radiation) are generally recognized as the proximate causes of such degradation. Most of these, except solar radiation, are most damaging to aircraft on or near the ground, where military aircraft spend the bulk of their time as contrasted with commercial aircraft. Operational factors, conditions relative to aircraft utilization, such as flying hours, payload, altitude, mission profile, pilot skill and general tidiness of flight crews also contribute to accelerated degradation of aircraft. Other contributing factors are maintenance, accidents and design problems.

The term environmental degradation as used herein includes a variety of problems, including corrosion, stress-corrosion cracking, and more. As used herein, corrosion includes all of the foregoing.

The extent of corrosion damage and the related need for maintenance and repair varies substantially from one aircraft to another. These variations are most visible at depot maintenance where nearly identical aircraft in terms of age, flying hours, and other traditional indices of age are observed to be strikingly different with respect to corrosion.

It has been reported that corrosion maintenance costs the Air Force approximately one billion dollars a year, therefore, there is a need for improvements in corrosion prevention, corrosion detection and repair of corrosion damage. Much of these costs can be directly attributed to corrosion inspection procedures. Corrosion is costly and the most destructive airworthiness-related maintenance problem facing the maintenance of a fleet of a military aircraft. Corrosion is extremely difficult to predict, prevent and detect non-destructively early in its formation. For example, access to corroding areas is frequently difficult or impossible, making conventional, non-destructive evaluation techniques generally inadequate to; detect such corrosion. Thus, costly and potentially destructive structural disassembly is frequently required to detect and evaluate the extent of airframe corrosion. Approximately twelve percent of an aircraft's life is spent in some form of maintenance or inspection procedure, thus, if maintenance and inspection time can be decreased and aircraft availability increased, the effective size of a fleet of aircraft can be correspondingly increased.

In the currently accepted corrosion inspection procedures, visual observation of the part being inspected is heavily relied upon, therefore, if corrosion occurs under paint it is very unlikely that such corrosion will be detected before substantial damage to a part has occurred. Many times corrosion cannot be detected under paint by visual examination until the paint blisters and the part is so corroded that it must be replaced. Additionally, the visual inspection methods currently being used to detect and control corrosion are very subjective and are highly operator dependent.

Infrared, non-destructive testing has been used in the past to inspect workpieces for internal defects and one method of doing so was described in U.S. Pat. No. 3,504,524. The method described in U.S. Pat. No. 3,504,524 involved spraying the workpiece with a vinyl base carrier of a carbon pigment to form a constant, high emissivity surface in the infrared region which is easily removed from the surface being tested. After application of the coating, the test surface is heated with a suitable source of radiant energy and the temperatures of successive spots on the test surface are determined by scanning the coated surface with a radiometer. Output from the radiometer is then transmitted to an oscillioscope or other display device where any flaws in the workpiece are displayed as infrared picture. U.S. Pat. No. 3,504,525 is particularly concerned with controlling the emissivity of the test surface at a standard level by applying a protective coating that has uniform radiating characteristics to the test surface. An essential characteristic of the coating applied to the test surface is that it is easily removed when the test is completed.

U.S. Pat. No. 3,020,745 also discloses the use of an infrared detector to test metal objects for flaws. In this method the area to be inspected is heated by induced eddy currents which uniformly increase the temperature of the test surface in the absence of flaws. At a flaw, the induced current is concentrated about the edges or corner of the flaw and a hot spot develops which is detected by an infrared detector. This method requires that the test surface be covered with a thin homogeneous coating having a high emissivity. U.S. Pat. Nos. 4,037,473; 3,314,293 and 2,846,882 also disclose the use of infrared detectors to measure the temperature of a workpiece. Additionally, the use of infrared thermography as an inspection tool is discussed in "Troubleshooting Products through Infrared Thermography" which appeared in the Nov. 10, 1983 issue of Machine Design. This paper points out that thermography can be used to characterize a complete temperature field around a particular point of interest. It also points out that only surface temperatures can be measured by this technique and that accurate readings are hard to obtain from shiny surfaces.

DISCLOSURE OF THE INVENTION

Accordingly, it is an object of the present invention to provide a corrosion detection method and apparatus which are applicable to an assembled aircraft and which do not require structural disassembly of the aircraft being tested.

Another object of the present invention is to provide a corrosion detection method and apparatus employing infrared thermographic techniques to detect any localized temperature difference in the area of the aircraft being tested for corrosion, thus indicating the presence of corrosion beneath the aircraft's surface coating.

The principal feature of the present invention is the provision of a totally new approach to the detection of corrosion in aircraft, aircraft components, structures, substructures and the like, such detection currently being accomplished in the art by means of disassembly and visual inspection. In accordance with the present invention, a method and apparatus are provided for detecting corrosion in aircraft, aircraft components, structures and the like. The method utilizes infrared thermographic analysis and comprises the steps of applying a pulsed infrared heat input to the test surface and detecting variations in thermophysical properties of the surface being tested with thermographic imaging techniques.

Another feature of this invention is the provision of a video campatible infrared thermal imaging scanner for detecting variations as described. The scanner is a small, light-weight, portable field instrument that produces a television compatible video output signal of the thermophysical characteristics it is viewing. The viewed scene is displayed on either a black and white or color monitor and may be recorded for permanent retention by a video cassette recorder (VCR).

In addition to the feature of video compatibility, the invention is further characterized by the simplicity and ease with which the test surface is subjected to infrared radiation. In accordance with the present invention, infrared radiation is directed against the surface of the coated metal to be inspected from an infrared lamp in pulses by, for example, combining the infrared lamp with a mechanical or electrical shutter mechanism so that the frequency and duration of the pulses will be known. The radiation may also be pulsed using an electronic or other type control that alternately turn the power source off and then on again. The frequency and duration of the pulses are determined based upon the physical and chemical characteristics of the test piece. The pulsed radiation raises the temperature of the coated metal surface being tested to a temperature above its normal ambient. After the temperature of the test piece has been raised above its normal ambient corroded areas are detected under any coating which might be covering the test surface as localized hot spots because the thermal conductivity of sound metal is higher than the conductivity of metal oxides. The pulsing of the infrared radiation as it is applied to the surface being viewed (image surface) provides for intervals during which the test piece is not being heated by application of radiant energy thus allowing the test surface to cool somewhat as heat is conducted away from the surface thereby creating localized temperature differentials between heating areas and corroded areas.

Yet another important feature of the present invention is the ability of the scanner to be fitted with a variety of optical accessories including view expanding lenses, close-up lenses and telescopic lenses. This provides the capability of viewing a potential corrosion site from a distance without the need for the inspector to be in close proximity to the inspection site.

Still another feature of the present invention is the provision of a sighting means for visually indicating to the operator the particular area of the aircraft being tested for corrosion that is being viewed by the scanner. In accordance with one embodiment of the invention, the sighting means takes the form of a hand-held pointer or more perferably, a laser mounted on the scanner so as to mark the test site being viewed by the scanner with a beam of light.

Another important feature of the present invention is the provision of an auto-focus, low-light video camera which has a remote control zoom lens to provide an operator with television-like visual display of the area being scanned.

Another useful feature of the present invention is the remote control pan and tilt capability of the scanner. Certain areas of an aircraft are often either inaccessible to an inspector or difficult to reach, therefore, the ability to remotely locate and position the scanner makes the inspection procedure easier and more efficient.

Yet another feature of the present invention is the ease with which the combination of optical scanner lenses, laser pointer, video camera and remote control pan and tilt capability allows the operator to inspect an aircraft for corrosion.

A very important feature of the present invention is the capability of the scanner to detect corrosion regardless of the emissivity of the test surface, thereby eliminating the need to coat the test surface with a constant emissivity coating prior to inspecting for corrosion. This also eliminates the need for time consuming cleanup after the inspection is complete.

Another important feature of the present invention is the provision of a scanner capable of viewing the irradiated surface simultaneously with the application of thermal energy to the test piece.

Another feature of the present invention is the provision of a real time thermal map of the image surface of the test piece.

Another feature of the present invention is the provision of means such as a video cassette recorder to record for permanent retention a thermal map of every aircraft inspected thereby creating a corrosion history of each inspected aircraft which can be used to predict future maintenance needs.

A very important feature of the present invention is the provision of color imaging capability. The ability to view the thermal map of the test area in color greatly enhances the sensivity of the procedure thus making it possible to detect very small common sites.

One advantage of the present invention is that this method can be applied to any metal in any configuragion in either a coated or an uncoated condition. While the inventors' use of this method will be largely to test aircraft, the invention has broader applicability.

Another advantage of the method and apparatus of the present invention is the elimination of the need for destructive structural disassembly of aircraft being inspected for corrosion.

Another very important advantage of the method and apparatus of the present invention is substantially increased sensitivity. The method and apparatus of the present invention are approximately 100 times more sensitive than other techniques and apparatus.

Still another advantage of the present invention is that the appratus is man-portable. This portability allows the apparatus to be removed from depot maintenance shops and put in the field and operated by not more than two men.

In accordance with these and other objects, features and advantages of the present invention. There is provided an emissivity independent method for detecting corrosion in aircraft under any paint or coating using infrared thermography; the method comprising the steps of directing pulses of infrared radiation onto the surface being inspected so that the temperature of the test surface is raised above its ambient; scanning the irradiated surface with a sensing device to detect any localized temperature differentials which might be present on the test surface; converting the sensed differentials into a signal representative of the intensity and location of the temperature differential on the test surface; transmitting the signal to a video display means and displaying the signal as a thermal map of the area being inspected.

In accordance with the present invention, the method further comprises the steps of providing a source of infrared radiation of a first wavelength and directing pulses of radiation from the provided source onto the surface being inspected to raise the temperature of the inspected surface above its normal ambient. The duration and the intensity of the radiation pulses aimed at the test surface are relative to the thickness of the metal being tested, any coating present thereon and to the thermal conducivity of the metal being tested and in usual practice they usually are at least equal to and sometimes exceed the internvening periods in which no radiant energy is directed toward the test surface.

The method of the present invention further comprises the steps of sensing the rate at which the irradiated metal cools during the zero radiation periods between pulses of radiation with a radiometer sensitive to infrared radiation having a wavelength different from that of the radiation generated by the infrared source, converting this sensed radiation into a video compatible signal representative of the cooling rate of the object being inspected, and transmitting the signal to a video display apparatus.

The method of the present invention further comprises the steps of directing pulses of infrared radiation having a first wavelength onto a surface of a metal object being inspected for corrosion and adapting the frequency and duration of the radiation pulses to the thermal conductivity of the metal being inspected so that after the temperature of the test surface is raised above its normal ambient, heat is conducted away from the test surface at a rate which is greater than the rate at which radiant energy is being directed upon the test surface.

The method of the present invention also comprises the step of scanning the imaging surface of the object being inspected for corrosion with an infrared detector to measure temperature differentials occurring on the imaging surface which may be characteriized by capturing infrared radiation of a second wavelength that is being emitted from the imaging surface during the intervals between pulses of infrared radiation which are being generated by the infrared source.

The method of emissivity independent infrared corrosion inspection which also comprises the steps of varying the frequency and duration of the radiation pulses as well as the intensity of the pulsed radiation in relation to the thermal conductivity of the metal being irratiated so that the temperature of the irradiated surface is raised above its normal ambient heat is conducted away from the non-corroded areas of the surface being viewed at a rate greater than the rate at which radiation is being applied to that surface and heat is being conducted away from corroded areas on the same surface at a rate less than the rate of irradiation.

The present invention also comprises apparatus for the emissivity independent thermographic detection of corrosion on coated metal surfaces which comprises means for applying radiant energy to the image surface of the metal; means for scanning the image surface of the metal for infrared radiation being emitted therefrom and means for capturing the emitted radiation and converting it into a signal representative of the thermophysical characteristics of the surface being inspected; and means for visually displaying the signal as a thermal map of the test surface.

In accordance with the present invention, the means for applying radiant energy to the image surace is generally an infrarcd source adapted to generate pulses of infrared radiation of predetermined frequency and duration. The pulses of energy can either be produced by using an electronic or mechanical shutter mechanism or either electronic or mechanical means to interrupt the flow of power to the infrared generator.

Further, in accordance with the present invention, the scanning means is a scanning camera capable of detecting and capturing infrared radiation within a specific wavelength band. The camera also includes an electro-optical transducer for converting the captured radiation into an electrical signal. The camera is also coupled with an infrared signal processor which converts the electrical signal into a video compatible signal representative of the thermophysical characteristics of the image surface.

Further, in accordance with the present invention, the signal produced by the infrared signal processor is displayed as a thermal map of the image surface. The monitor may be either a color monitor or black and white, however, the video display when produced in color provides a more distinctive and more easily interpreted representation of the thermal characteristics of the image surface. The viewed thermal patterns are recorded for permanent retention on a video cassette recorder (VCR) or other similar device. When color processing is used, color enhancement electronics are provided to allow an operator to continuously observe temperature zones within the scene displayed. When this technique is used, each color represents a different isotherm range.

Also in accordance with the present invention, the infrared generator (source) is adapted to allow the operator to vary the intensity of the radiation being directed aginst the image surface.

The apparatus further comprises a sighting means for visually marking the image surface that is being viewed by the scanning camera. The sighting means preferably takes the form of a laser mounted on the scanning camera so that the site being viewed by the scanning camera is illuminated by a beam of light.

BRIEF DESCRIPTION OF THE DRAWINGS

These and other objects, features and advantages of the present invention will become more readily apparent as the description proceeds with the following more particular description of the preferred embodiment of the present invention, the apparatus portions of which are illustrated in the accompanying drawings. The drawings in which like reference characters indicate corresponding parts in all views, are not necessarily to scale, emphasis instead being placed on illustrating the principles of the invention.

FIG. 3A is a photograph of the specimen shown in FIG. 2A showing the thermal characteristics of the specimen when steady state infrared radiation is applied to the back side of the specimen.

FIG. 3B is a photograph of the specimen shown in FIG. 2A showing the thermal characteristics of the specimen as they appear when steady state infrared radiation is applied to the image side of the specimen.

FIG. 4A is a photograph of the specimen shown in FIG. 2A showing the thermal characteristics of the specimen where pulsed infrared radiation is applied to the image side of the specimen.

FIG. 4B is a photograph of the specimen shown in FIG. 2B showing the thermal characteristics of the specimen when pulsed infrared radiation is applied to the image side of the specimen.

FIG. 4C is a photograph of the specimen shown in FIG. 2B depicting the thermal characteristics of the specimen when steady state infrared radiation is applied to the image side of the specimen.

BEST MODE OF CARRYING OUT THE INVENTION

Figure 1:
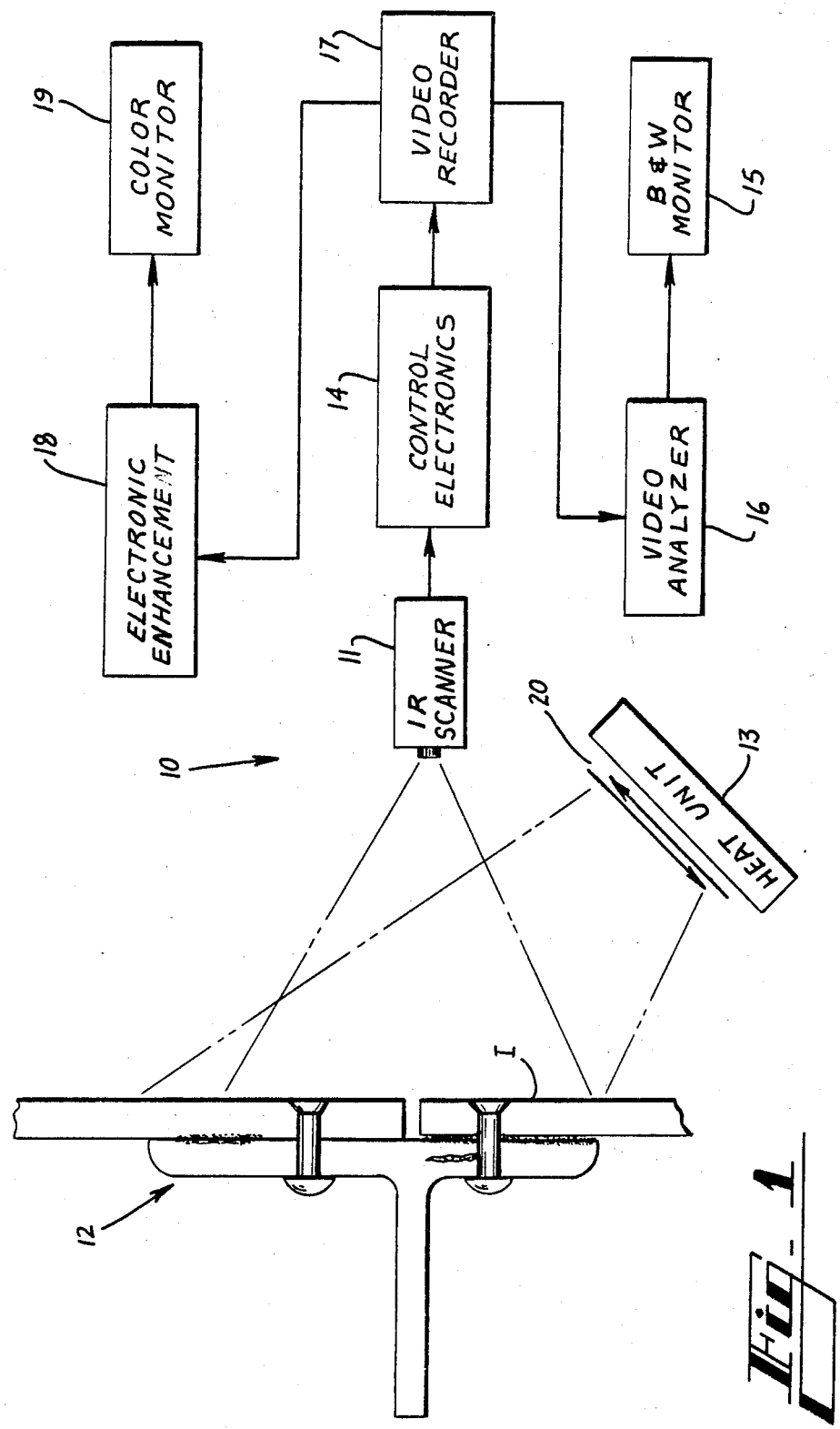
FIG. 1 is a schematic representation of the apparatus of the present invention including a partial cross-section of an airframe structural specimen.

Referring to FIG. 1, the apparatus of the present invention, generally indicated by the numeral 10, is illustrated in block diagram form in relation to a partial crosssection of an airframe structural specimen 12. In its simplest form, the apparatus 10 comprises a high resolution infrared scanner 11 which comprises a high resolution infrared scanner 11 which captures infrared radiation emitted from the image side I of an irradiated airframe structural specimen 12. Infrared radiation is emitted from specimen 12 because the temperature of specimen 12 has been raised above its normal ambient by application of infrared radiation to it from heat unit 13. The radiation from heat unit 13 is applied to specimen as pulses of electromagnetic waves by using shutters 20 in the infrared portion of the spectrum so that any corrosion on the specimen 12 can be visually characterized and displayed without the necessity of resorting to structurally damaging disassembly. As specimen 12 heats to a temperature above its normal ambient it in turn emits infrared radiation representative of its thermophysical characteristics. When this infrared radiation is captured by scanner 11 it is converted into a video compatible signal that is transmitted to control-electronics unit 14 for display on a black and white monitor 15. Also included is a video cassette recorder (VCR) 17 for recording, for permanent retention, the image created from the infrared radiation captured by scanner 11. As will be explained in more detail hereinafter, the output of VCR 17, is inputted, for example, to video analyzer 16 of the type manufactured by Interactive Video Corporation which permits a pictel by pictel analysis of the image with a sensitivity of approximately 0.02° C. for display on black and white monitor 15. The output of VCR 17 is also inputted, for example, to an electronic enhancement arrangement 18 for color enhancement of the signal for display on color monitor 19. Scanner 11, which comprises, for example, a Model 525 Infrared Thermal Imaging Scanner produced by Inframetrics, Inc., 25 Wiggins Avenue, Bedford, MA 01730, utilizes two low inertia mirrors to scan the image side I of the specimen 12 at television rates. An infrared detector, for example, a liquid nitrogen cooled mercury cadmium telluride ($H_gC_c+T_e$) detector, converts naturally admitted infrared radiation to an electrical signal which is employed to construct a television picture of the temperature pattern of the image side I of test specimen 12 by means of the control-electronic unit 14 with a sensivity of about ±0.2° C.

Control-electronics unit 14 provides the basic display functions of the system. The image, FIG. 4A, can be displayed as a normal television picture with brightness and tone of the displayed pattern indicating temperature difference in accordance with a calibrated gray scale. Alternatively, constant temperature contours are intensified over the normal image for selected temperatures, with a marker at the left of the display indicating the temperature differential as a fraction of the temperature range setting. The normal picture can also be displayed with a brightness line indicating the vertical position of a continuous horizontal scan wherein the temperature versus horizontal position is displayed for a continuous horizontal scan fixed in the image vertically by the brightness line. Alternatively, colorizing can be added to the display, as will be described in more detail hereinafter, which allows the operator to continuously observe temperature zones within the image, each color representing a different isotherm range.

Figure 5:
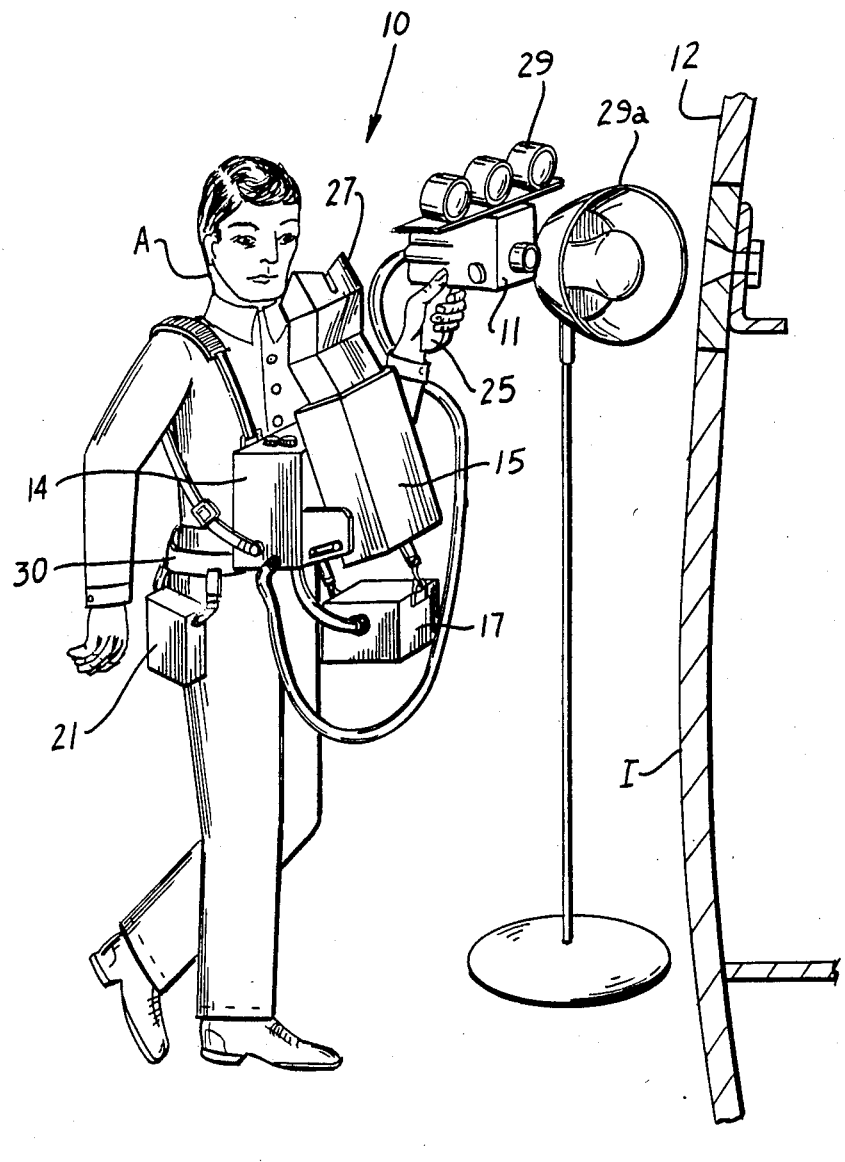
FIG. 5 is a perspective view illustrating the method and apparatus of the present invention with the apparatus in the portable configuration.

FIG. 5 shows the apparatus 10 in the portable configuration. In this configuration the apparatus 10 is carried by operator A by means of harness set 30. Battery 21 is provided to power apparatus 11. A video cassette recorder (VCR) 17 records, for permanent retention, the image created from the infrared radiation captured by scanner 11 having handle 25, a tripod mounting adapter (not shown) for scanner 11 a viewing hood 27 for monitor 15 are provided for as well as a camera adapter (not shown) for attaching a photographic camera to monitor 15 thereby permitting the photographing the image displayed on monitor 15.

Apparatus 10 further comprises a source of infrared radiation 29 for directing infrared radiation onto specimen 12, for example, the skin of an aircraft fuselage, to be inspected for corrosion. The source of infrared radiation 29, in this embodiment a bank of lights emitting radiation in the 0.5 to 2.5 micron wavelength band, is used to directly irradiate the image side I of the specimen 12 thereby raising the specimen temperature above its normal ambient. Radiation is applied to the specimen 12 in pulses or bursts of a frequency and duration so related to the thickness and thermal conductivity of the specimen to cause temperature differentials to occur as heat is conducted away from the surface of specimen 12 by sound metal. This occurs because the thermal conductivity of sound metal is greater than the thermal conductivity of the metal oxides which comprise the sought after corrosion.

Returning to FIG. 1, the method of the present invention will be explained in more detail. As shown in FIG. 1, the method comprises the steps of irradiating the image surface I of a test specimen 12 with infrared radiation from the band having a wavelength of from about 0.5 to about 2.5 microns in pulses or bursts until the temperature of the image surface I of specimen 12 is raised to a temperature above its normal ambient. By applying the infrared radiation in pulses which are relative to the thickness and thermal conductivity of specimen 12 temperature differentials are set up between corroded areas and non-corroded areas on the specimen because sound metal will conduct heat away from the surface I at a faster rate than will corroded metal. Likewise, temperature differentials will occur between areas of corrosion of different magnitude because less corroded metal conducts heat away from surface I at a higher rate than heavily corroded metal. Simultaneous with the application of radiation to surface I, scanner 11 is used to view surface I and capture infrared radiation emitted therefrom. Scanner 11 is adapted to capture radiation in the 8 to 12 micron wavelength of the electromagnetic spectrum and is blind to the radiation being used to heat surface I thereby making the method of the present invention substantially emissivity independent because scanner 11 will not capture background or reflected radiation. The radiation captured by scanner 11 is representative of the thermophysical characteristics of the specimen 12 and can be converted into a video compatible signal by control electronics 14 and displayed on monitor 15 as a thermal map or thermograph of the specimen surface. Interpretation of this thermograph allows the operator A, FIG. 5, to pinpoint exactly the location and intensity of corrosion on specimen 12 whether or not the corrosion is hidden from view by paint or similar coating. The wavelengths picked for the irradiating and viewing portions of the method were selected because of the temperature range being viewed when scanning surface I for temperature differentials. It is generally accepted within the infrared art that when temperatures below 1000° C. are being observed more photons of energy are available in the 8 to 12 micron wavelength portion of the spectrum, therefore the sensitivity of the method is increased by locating the scanning band in that portion of the spectrum that has the most detectable radiation for the temperatures being observed. The 0.5 to 2.5 micron band was then chosen as the irradiating or heating band because of the desire to make the method emissivity independent.

While the portable version of the apparatus 10 has been shown with a portable radiation source 29 mounted on top of scanner 11 a more preferred embodiment would use a remote radiation source 29A which is offset from the scanner 11. Additionally, in the preferred mode of practicing the present invention, scanner 11 is also offset from the perpendicular when viewing the image side I of specimen 12. It has been found that heat from the operator's body will reflect off surface I and will be picked up by scanner 11 as a ghost image. Likewise, if scanner 11 is held at a 90° angle in relation to image surface I, a cold spot will be indicated on the resulting thermograph which is a reflection of the scanner itself. Therefore, both the radiation source 29 and scanner 11 should be offset somewhat from the perpendicular when inspecting specimen 12 in order to reduce the influence of reflected energy sources. In order to accomplish this best mode of practicing the present invention, remote and free standing radiation source 29A is generally used. It is also more expedient to use either semi-portable or fixed energy source 29A because the amount of power required to operate the energy source requires the use of heavy cable therefore substantially eliminating the use of portable units because required power cables make the test apparatus bulky and difficult to manage.

Figure 6:
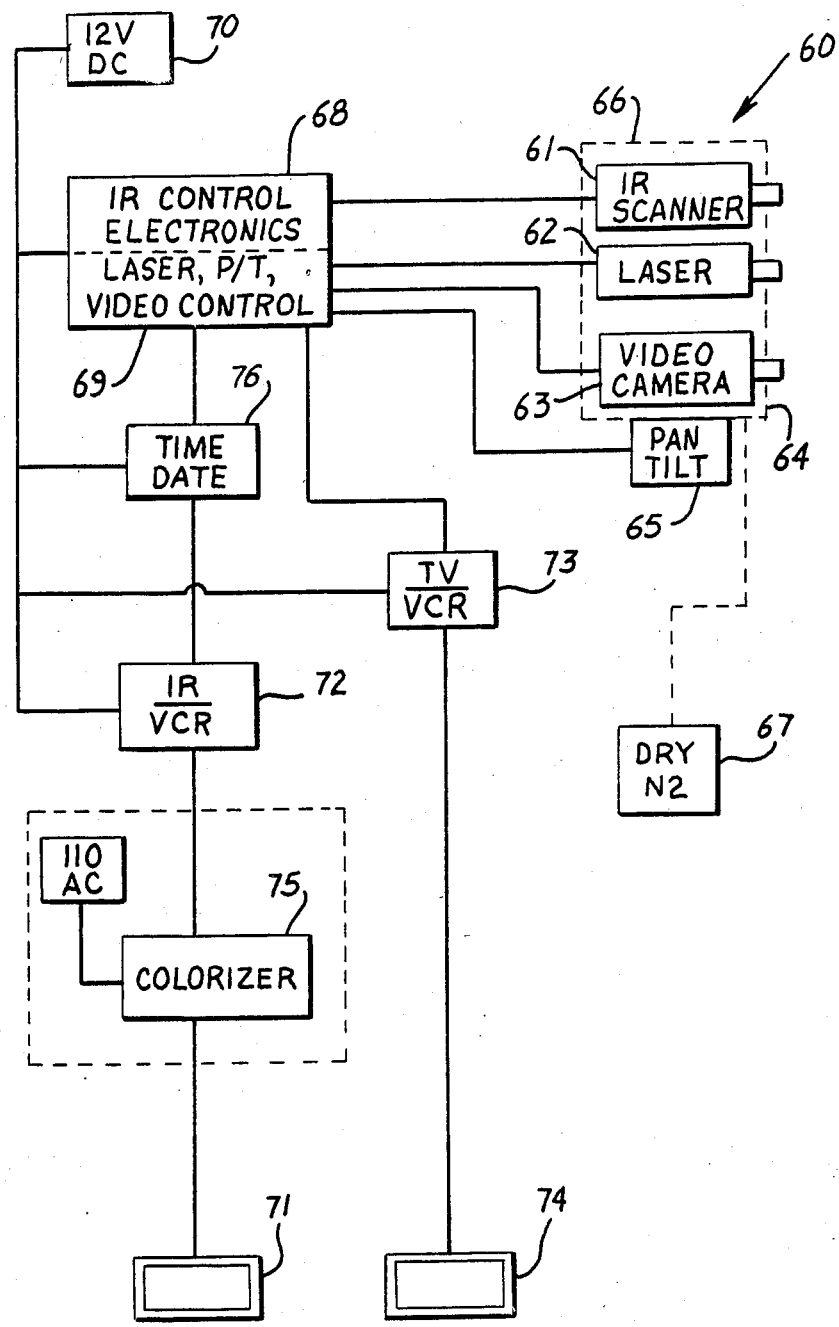
FIG. 6 is a schematic representation of another configuration of the present invention.

It should be understood that the method of the present invention is applicable to subassemblies as well as fully assembled aircraft. It should also be understood that the method of the present invention is in fact applicable to any painted or unpainted metal surface, for example, petroleum storage tanks, hulls and bulkheads of ships or oil well drilling rigs. When used to inspect such structures as well as assembled aircraft the apparatus not only includes the components previously discussed but might additionally include the components schematically described in FIG. 6. The apparatus includes a scanner assembly generally indicated at 60, which comprises an infrared scanner 61, a laser pointer 62 for visually marking the site viewed with a beam of light and a video camera 63 having auto focus and remote zoom lens capabilities to provide an operator with a video display of the image viewed by the scanner 60. Each of the components is compactly designed and individually, as well as removably mounted, to a platform 64 which is operatively associated with a pan and tilt arrangement 65 for remotely locating the scanner 61, pointer 62 and camera 63 as will be described more fully hereinafter.

When scanner 61 is to be used in volatile, explosive or corrosive environment, such as, for example, a fuel tank, an optional enclosure 66 and dry nitrogen gas purge system 67 are provided to surround the electrical components of the apparatus with an atmosphere of substantially inert gas. This arrangement minimizes the possibility of explosion due to an electrical discharge or spark and thus render the equipment intrinsically safe. Additionally, this arrangement minimizes damage to the electrical equipment in the apparatus should the atmosphere of the site of the inspection be corrosive.

Remotely located from the scanning assembly 60 are the infrared scanner control-electronics unit 68 and the laser, pan and tilt and video controls 69. A 12 volt D.C. battery 70 is used to power controls 68 and 69 when the apparatus is operated in the remote control mode. A date-time generator 76 provides a time and date of the inspection which is displayed on monitor 71. Also included is an IR VCR 72 which provides a permanent record that the test displayed on television monitor 71. Also included is an IR VCR 72 which provides a permanent record of the test as well as a TV VCR 73 connected to a second monitor 74 which provides a permanent record of the images viewed by camera 63 during the test procedure.

An optional colorizer 75 can be inserted between the IR VCR 72 and monitor 71 in order to permit the operator to continuously observe temperature zones within the image, each color representing a different isotherm range. In lieu of a colorizer, a computer enhancement arrangement of the type manufactured by Interactive Video Corp. may be used and allows a pictel by pictel analysis of the image with a sensitivity of approximately 0.02° C. The computer enhancement arrangement provides analysis in real-time or alternatively, from a tape recording of the test using IR VCR 72. Thus, taping of the scanner signal to IR VCR allows for later color enhancement or computer analysis, such later computer analysis being impossible if the signal is first recorded with color enhancement. In use, scanner assembly 60 is located adjacent to a specimen to be inspected for corrosion.

Figure 2B:
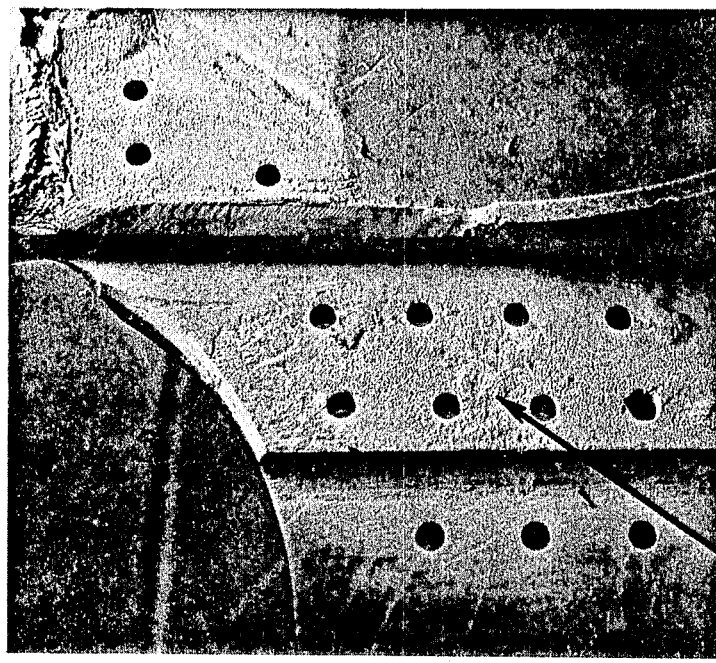
FIG. 2B is an ordinary light photograph of the specimen shown in FIG. 2A.
Figure 2A:
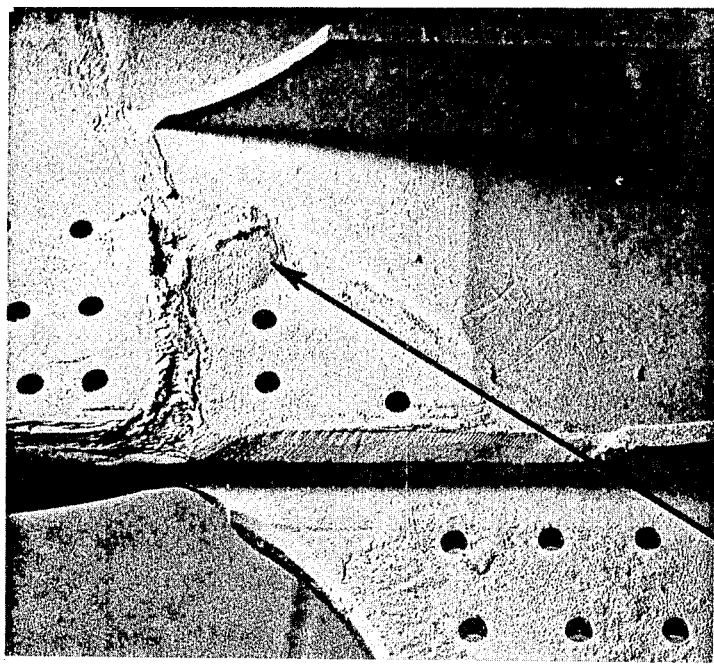
FIG. 2A is an ordinary light photograph of a test specimen.

FIG. 2A is an ordinary light black and white photograph of a test specimen having substantial corrosion at A. FIG. 2B is also a black and white photograph of the specimen shown in FIG. 2A with a slightly different image area. This photograph shows a portion of the corrosion at A but is primarily ilustrative of a second area of corrosion involvement B. The corrosion areas A and B were chosen because they illustrate corrosion which can be seen by ordinary visual inspection in ordinary light therefore making the comparison of the ordinary light and infrared images more illustrative of the ability of the method and apparatus of the present invention to detect corrosion and represent it as a thermal image.

To produce the image shown in FIG. 3B the specimen of FIG. 2A was subjected to a steady state infrared radiation on the image side and scanned by scanner 11 (FIG. 1) which captured infrared radiation emitted by the surface of the specimen. As can be readily seen the image fails to distinctly show the corroded area A. The constant application of heat to the specimen surface causes the specimen surface temperature to be fairly constant in the radiation target area. The darker areas around the periphery of the radiation target area show some surface cooling but do not present an accurate representation of the thermophysical characteristics of the specimen. When steady state infrared radiation is applied to the back side or non-image side of the specimen shown in FIG. 3A local hot spots appear as the light areas with cooler areas of the specimen being darker. The very light prints in the image area are areas of sound metal which readily conduct heat from the irradiated side of the sample to the image side. The smaller, more circular shaped light areas appear to be the holes which extend through the specimen and thereby allow the radiation to pass directly through the specimen to the scanner.

Referring now to FIG. 4A which is a black and white photograph of a video image produced by the practice of the present invention. In FIG. 4A the light area which appears at the left center depicts the corroded area A in FIG. 2A. As can readily be seen the areas of sound metal appear as the darker shaded areas because the surface heat build up which results from a pulsed application of radiation to the image surface is localized in the areas showing substantial corrosion involvement in the ordinary light photograph. This is explained by the lower thermal conductivity of the metal oxide which causes heat to be retained in the corroded area while it is rapidly conducted away from the image surface by sound metal. FIG. 4B demonstrates the same point. The thermograph of the specimen of FIG. 2B clearly shows the areas of corrosion found in area B as the white points on the dark background.

FIG. 4C demonstrates again that the steady state application of radiation to the image surface is inadequate to clearly distinguish corroded from non-corroded metal because heat cannot be conducted away from the surface at a rate which is high enough to contrast the hotter metal oxide areas B from sound metal areas.

Although the invention has been discussed and described with primary emphasis on one embodiment, it should be obvious that adaptations and modifications can be made without departing from the spirit and scope of the invention.

We claim:

1. A method of inspecting a coated metal object for corrosion comprising the steps of:
   (a) directing a series of pulses of infrared radiation, having a given wavelength, onto the coated metal object so that the temperature of said coated metal is raised above ambient;
   (b) scanning the coated metal object with a sensing device at the same time said series of pulses of infrared radiation are directed onto the coated metal object to detect and record any temperature differentials which might be present on said coated metal object;
   (c) sensing said temperature differentials and converting said temperature differentials into a signal representative of the intensity and location of said temperature differentials.
   (d) transmitting said signal to a video display means; and
   (e) displaying the signal on said video display means in the form of a thermal map of the coated metal object, so that areas of corrossion are identified.

2. The method of claim 1 wherein step (a) comprises the steps of:
   (a) providing a source of infrared radiation of given wavelength; and
   (b) directing a series of pulses of said infrared radiation onto said coated metal object, the duration of said pulses being relative to the thickness of said coated metal object and at least equal to the intervening periods of no energy which separate said pulses so that the temperature of the coated metal object is raised above ambient temperature.

3. The method of claim 1, wherein step (b) comprises the steps of:
   (a) sensing the rate at which said coated metal object cools during periods of zero energy with a radiometer sensitive to infrared radiation of a wavelength not equal to the given wavelength of the infrared radiation used to raise the temperature of the coated metal object, and;
   (b) converting said cooling rate into a signal repsentative of said cooling rate.

4. An emissivity independent method of inspecting a coated metal surface comprising the steps of:
   (a) providing a source of pulsating infrared radiation; having a first wavelength;
   (b) directing pulses of infrared radiation from said radiation source onto said coated metal surface so that the temperature of the coated surface is raised above ambient;
   (c) scanning the coated metal surface at the same time said pulses of infrared radiation are directed onto said coated metal surface with an infrared radiation detecting device for infrared radiation having a second wavelength to detect any temperature differentials which might occur on said surface as a result of exposure of said surface to said pulses of infrared radiation;
   (d) converting any detected temperature differentials into usable signals and displaying the same on a video display means in the form of a thermal map of said surface.

5. The method of claim 4, wherein step (b) comprises:
   (a) directing pulses of infrared radiation having said first wavelength onto a surface of a coated metal test piece; and
   (b) adapting the frequency and duration of said radiation pulses to the thermal conductivity and thickness of the test piece whereby after the temperature of the test piece is raised above its normal ambient, heat is conducted away from the test surface at a rate which is greater than the rate at which radiant energy is directed upon the test surface.

6. The method of claim 4, wherein step (c) comprises:
   scanning the coated metal surface with an infrared detector to measure temperature differentials occurring on said surface and which are characterized by infrared radiation of a different wavelength emitted from said surface during the intervals between said pulses of infrared radiation.

7. The method of claim 5, wherein step (b) comprises: varying the frequency and duration of said radiation pulses and the intensity of the pulsed radiation in relation to the thermal conductivity of the metal being irradiated whereby after the temperature of the irradiated surface is raised above its normal ambient, so that the heat is conducted away from non-corroded areas on said test surface at a rate equal to or greater than the rate at which said radiation is being directed against said surface and heat is conducted away from corroded areas on said surface at a rate less than the rate at which radiation is being directed against said surface.

8. The method of claim 4, wherein said first wavelength is from 0,5 to 2.5 microns.

9. The method of claim 4, wherein said second wavelength is from about 8 to about 12 microns.

10. The method of claim 5, wherein said radiation pulse frequency is in the range of approximately one pulse every 1/15 to 1/100 of a second.

11. An apparatus for the non-destructive identification and location of subcoating corrosion on a coated metal test surface which comrpises in combination;
(a) means for directing a series of pulses of infrared radiation onto the surface of said coated metal test surface;
(b) means for scanning the coated metal surface at the same time said series of pulses of infrared radiation are directed onto the surface for infrared radiation being emitted therefrom including means for capturing said radiation:
(c) means for converting said captured radiation into a signal representative of a thermal map of said surface; and
(d) means for visually displaying said signal as the thermal map of said surface, so that the locations of subcoating corrossion may be identified.

12. The apparatus of claim 11, wherein said means for directing said series of pulses of infrared radiation onto the surface of a coated metal test piece comprises source means for generating infrared radiation of a first wavelength and pulsing means for interrupting the infrared radiation being emitted from said source means whereby said infrared radiation is directed upon said coated surface in pulses of varying frequency and duration.

13. The apparatus of claim 11, wherein said means for scanning the coated metal surface of said test piece comprises scanning camera means capabale of detecting and capturing infrared radiation having a second wavelength, said camera means further including electrooptical transducer means for converting said radiation into an electrical signal.

14. The apparatus of claim 11, wherein said means for converting said captured radiation into a signal comprises an infrared signal processor means for converting said electrical signal into a video compatible signal repsentative of the thermal map of said surface.

15. The apparatus of claim 11, wherein said means for visually displaying said signal comprises video monitor means for converting said video compatible signal into the thermal map of said surface.

16. The apparatus of claim 11, wherein said means for visually displaying said signal comprises in combination video tape recording means and video monitor means.

17. The apparatus of claim 16, wherein said means for visually displaying said signal comprises in combination video tape recording means and color monitor means.

18. The apparatus of claim 12, wherein said first wavelength is from about 0.5 to about 2.5 microns.

19. The apparatus of claim 13, wherein said second wavelength is from about 8 to about 12 microns.

20. The apparatus of claim 12, wherein said pulsing means comprises shutter means for alternately closing and opening a path of radiation between said infrared source and said test surface at a desired frequency.

21. The apparatus of claim 12, wherein said pulsing means comprises electronic means for interrupting a flow of energy to said infrared source means in a periodic manner.

22. The apparatus claim 12, wherein said source means furthar includes means for varying the intensity of the infrared radiation generated by said source means.

* * * * *